(12) United States Patent
Schuehrer et al.

(10) Patent No.: US 6,705,541 B2
(45) Date of Patent: Mar. 16, 2004

(54) FRAGRANCE DISPENSER

(75) Inventors: Herbert Schuehrer, Bruchsal (DE); Klaus Renner, Ettlingen (DE)

(73) Assignee: Klocke Verpackungs-Service GmbH, Weingarten (DE)

( * ) Notice: Subject to any disclaimer, the term of this patent is extended or adjusted under 35 U.S.C. 154(b) by 0 days.

(21) Appl. No.: 10/230,401

(22) Filed: Aug. 29, 2002

(65) Prior Publication Data

US 2003/0085298 A1 May 8, 2003

(30) Foreign Application Priority Data

Aug. 30, 2001 (DE) ..................................... 201 14 352 U

(51) Int. Cl.$^7$ ................................................ A24F 25/00
(52) U.S. Cl. .............................. 239/34; 239/57; 239/36; 239/60
(58) Field of Search ............................... 239/34, 57, 36, 239/60

(56) References Cited

U.S. PATENT DOCUMENTS

| | | |
|---|---|---|
| 3,412,907 A | 11/1968 | Faso |
| 4,155,500 A | 5/1979 | Dutcher |
| 5,975,427 A * | 11/1999 | Harries ........................ 239/34 |
| 6,094,886 A | 8/2000 | Poignant |

FOREIGN PATENT DOCUMENTS

| | | |
|---|---|---|
| EP | 1 082 970 | 3/2001 |
| GB | 2 038 757 | 7/1980 |
| WO | WO 00/06464 | 2/2000 |

* cited by examiner

*Primary Examiner*—Dinh Q. Nguyen
(74) *Attorney, Agent, or Firm*—Browdy and Neimark

(57) ABSTRACT

A fragrance dispenser having a reservoir to receive an aroma carrier, the fragrances of which can escape at least partially through a dispensing opening when pressure is exerted onto the reservoir. The reservoir may have the shape of a bottle, wherein the dispensing opening, which is preferably designed as a snap-off opening, is disposed in the thinner region, i.e at the neck of the bottle. A packaging element preferably extends beyond the dispensing region of the reservoir, the packaging element being designed in that region in such a way that it interacts with a seal of the dispensing opening of the reservoir. The reservoir or packaging element may be designed as a free-standing package.

12 Claims, 10 Drawing Sheets

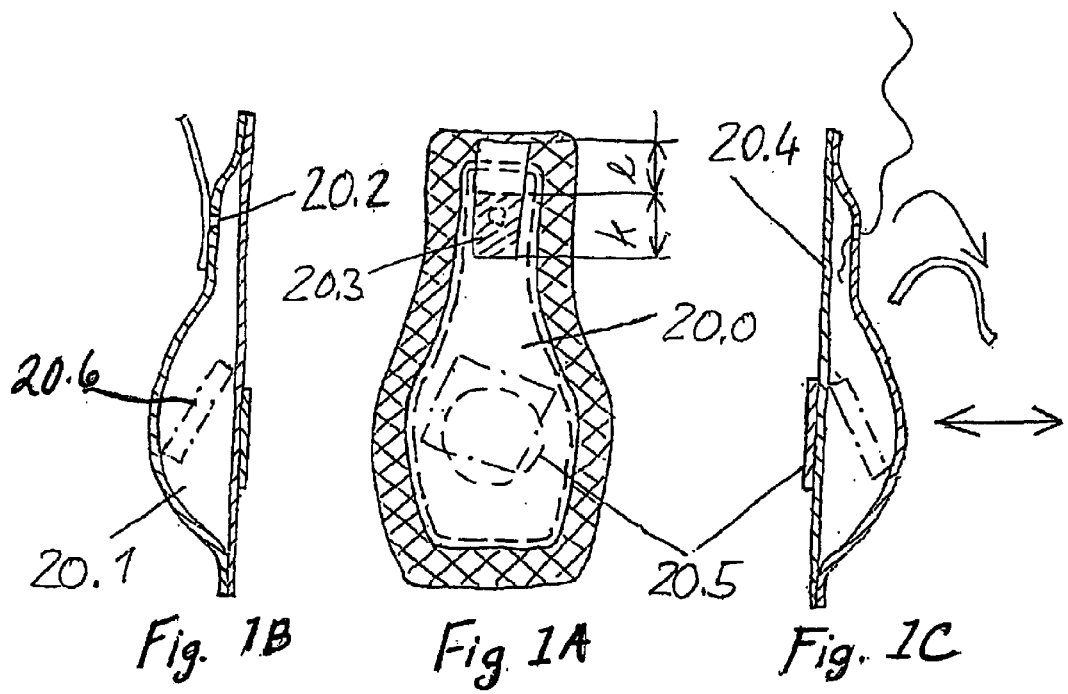
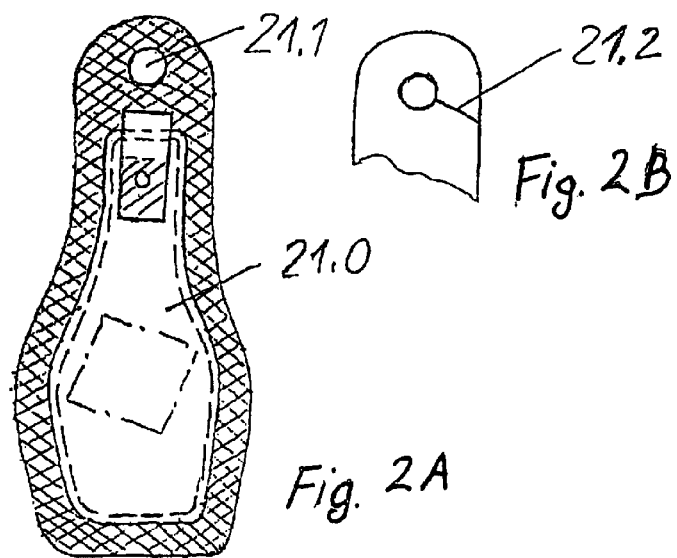

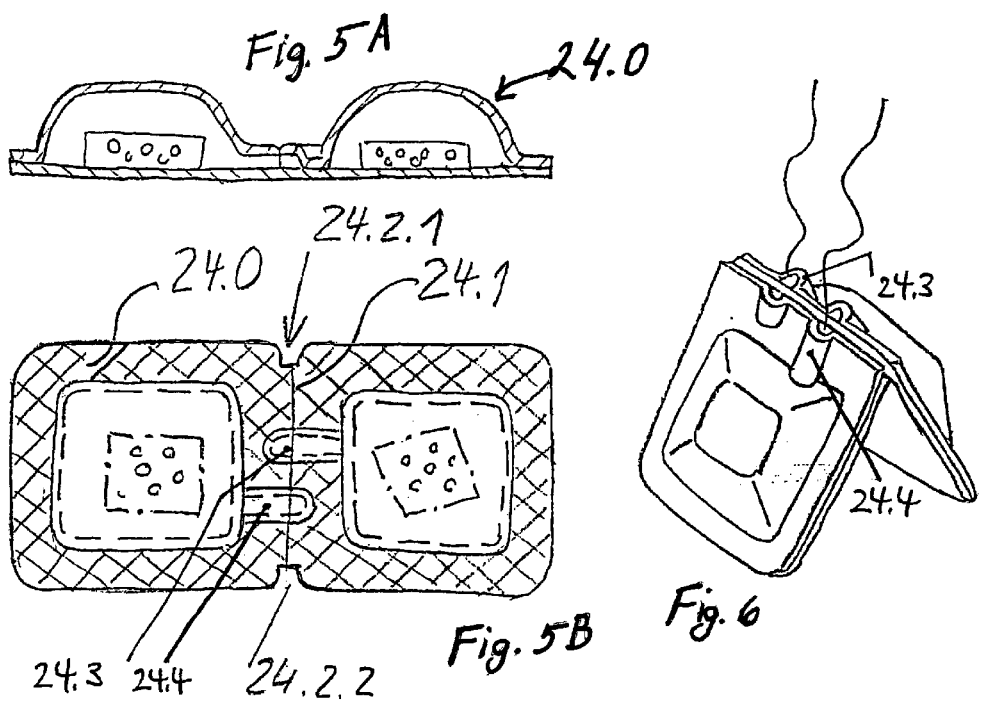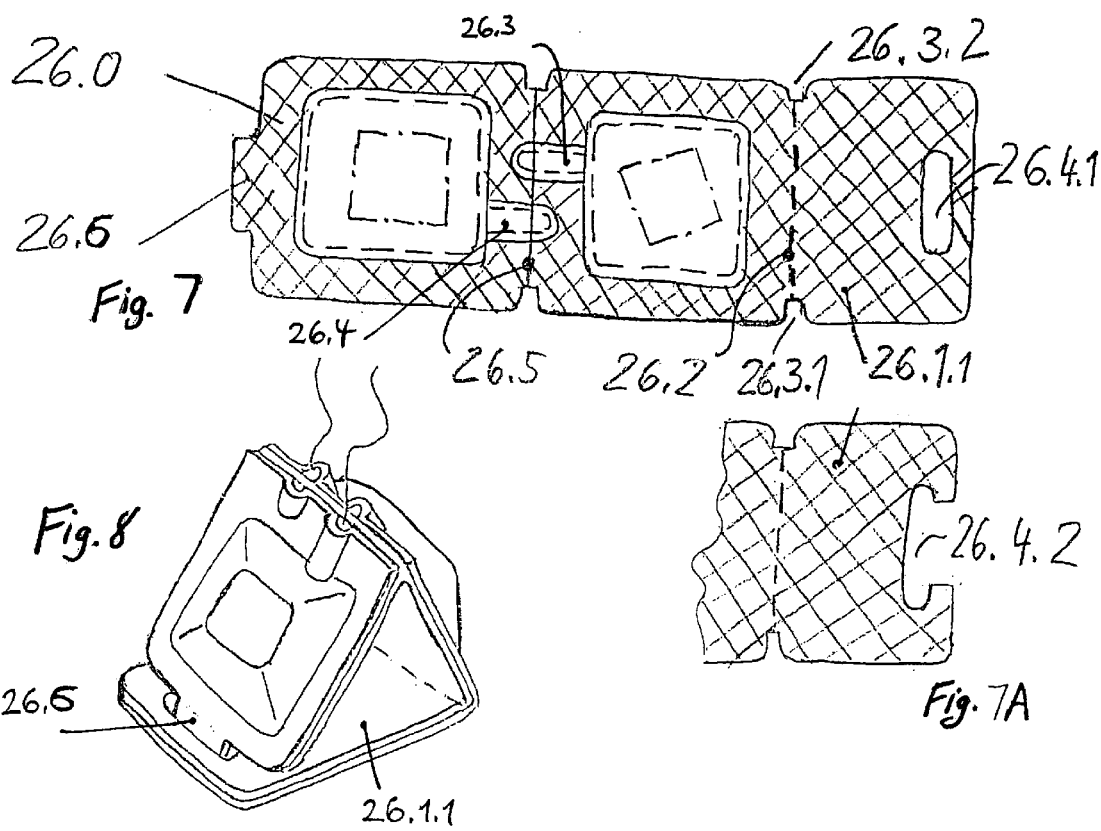

26.1.1

26.1.2

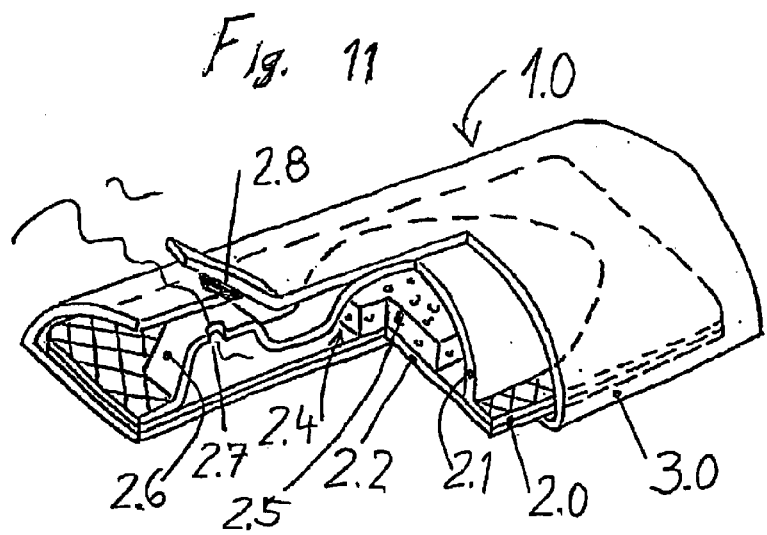
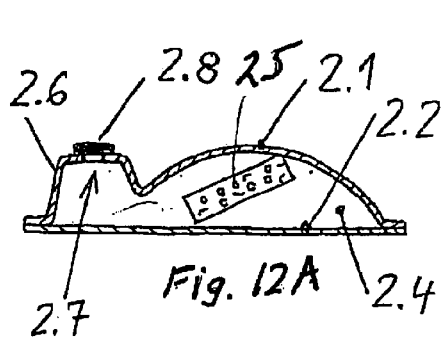
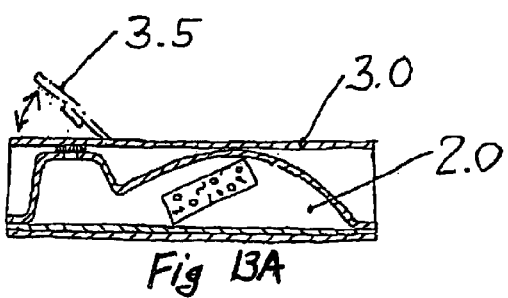
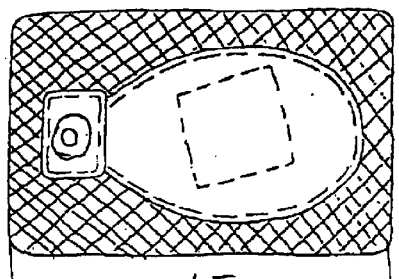
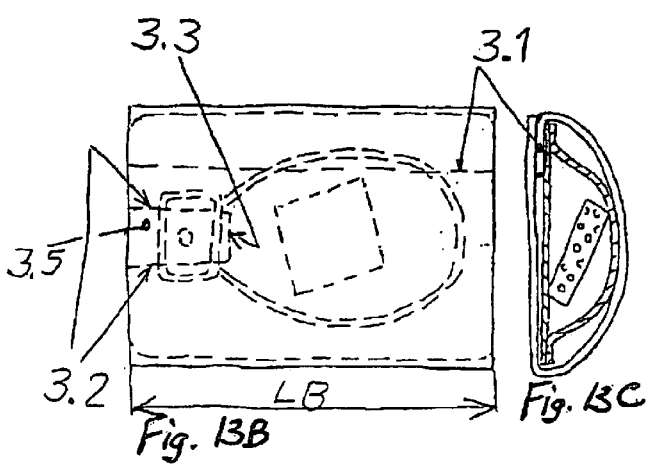

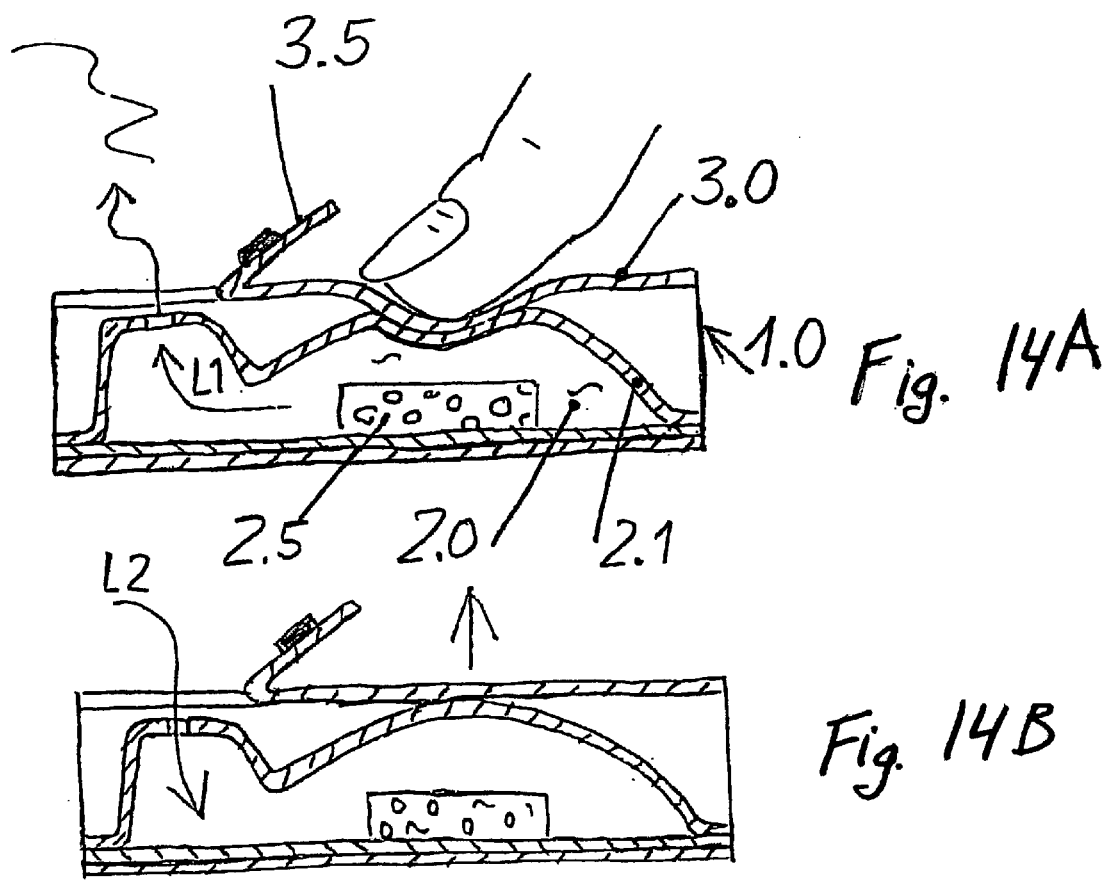

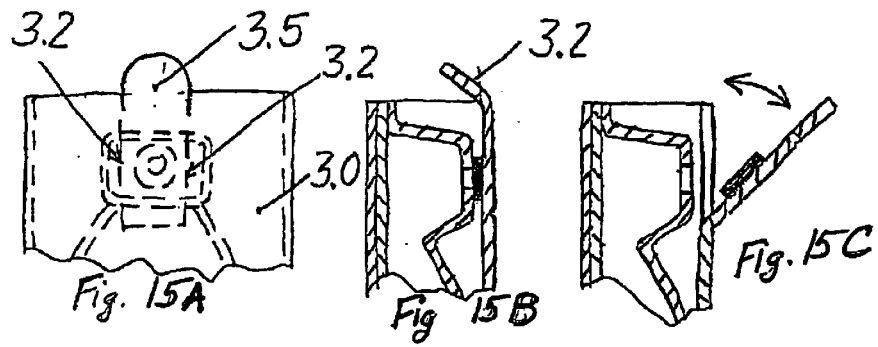
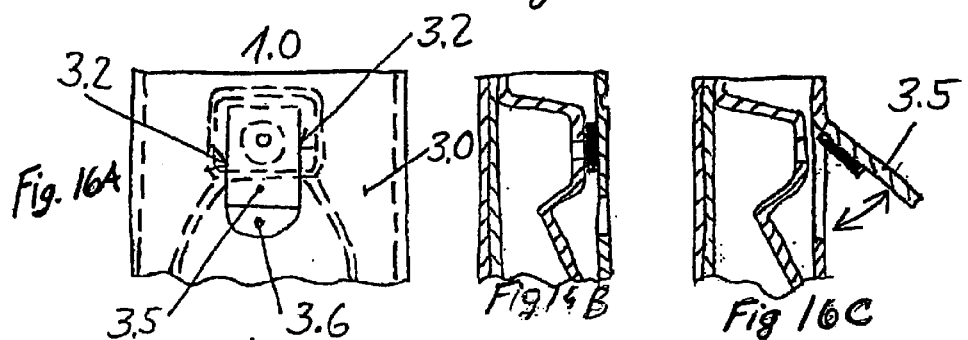
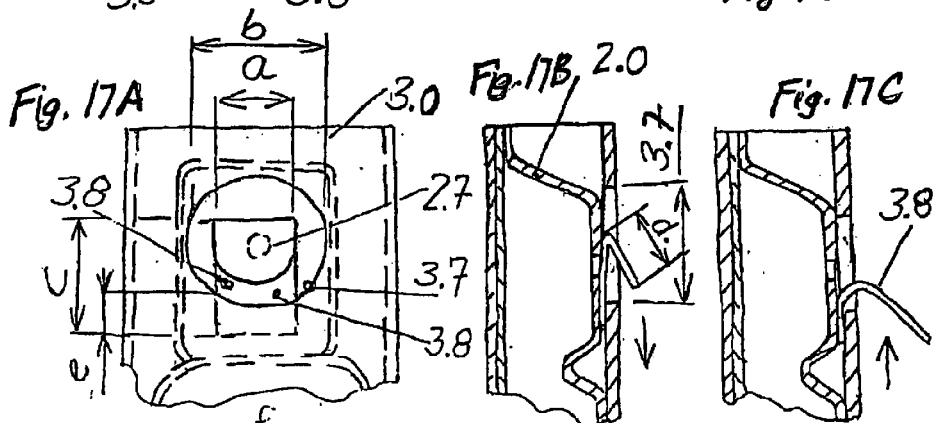
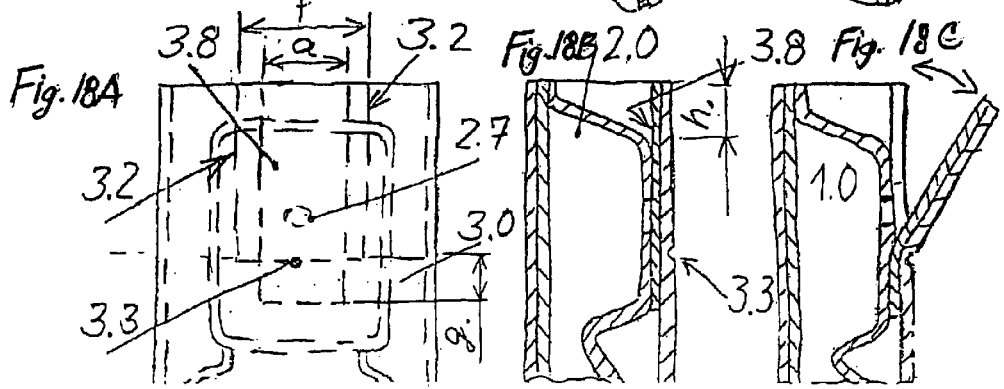

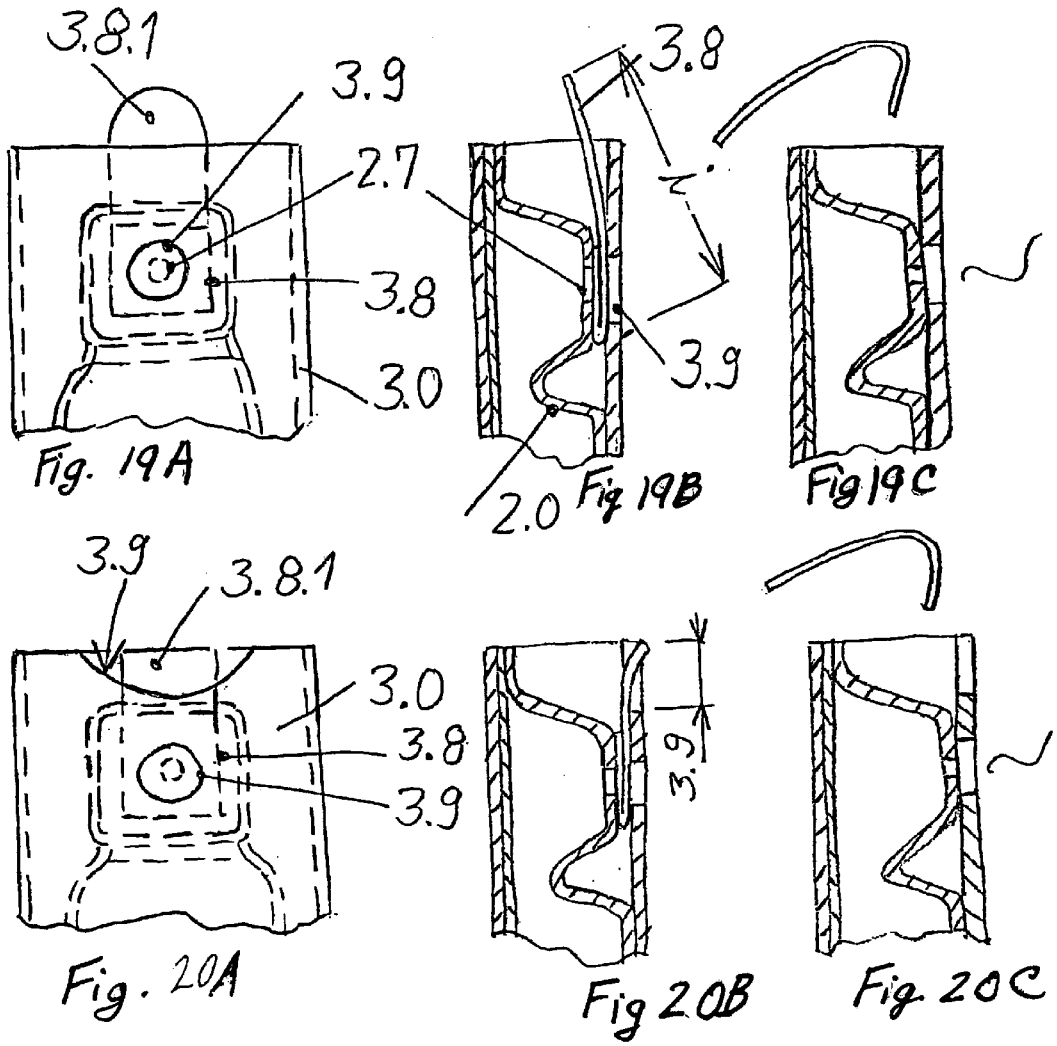

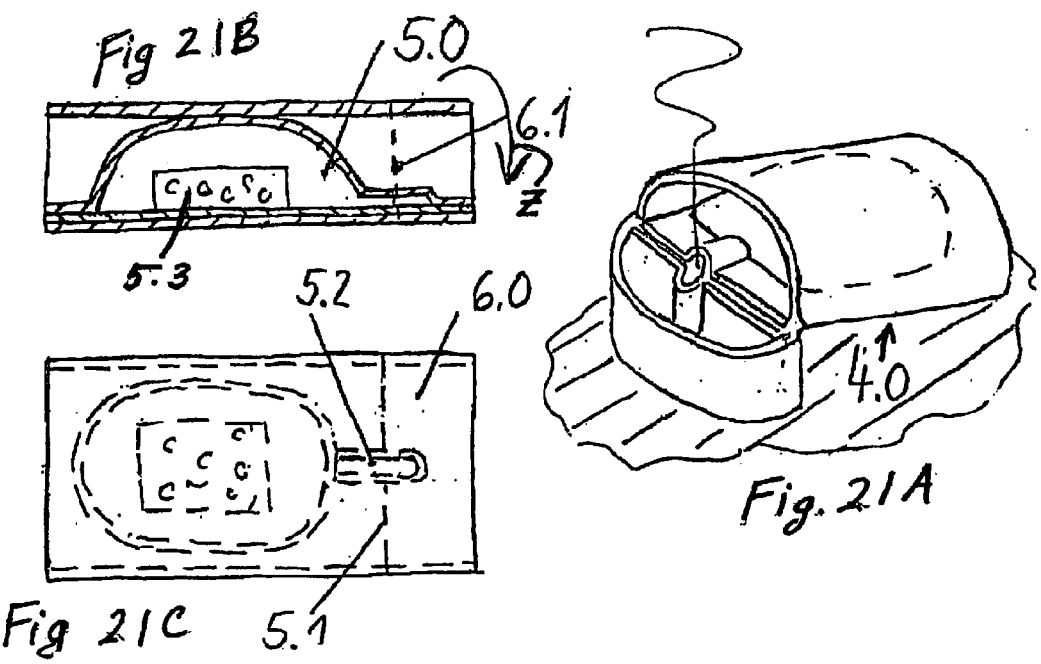
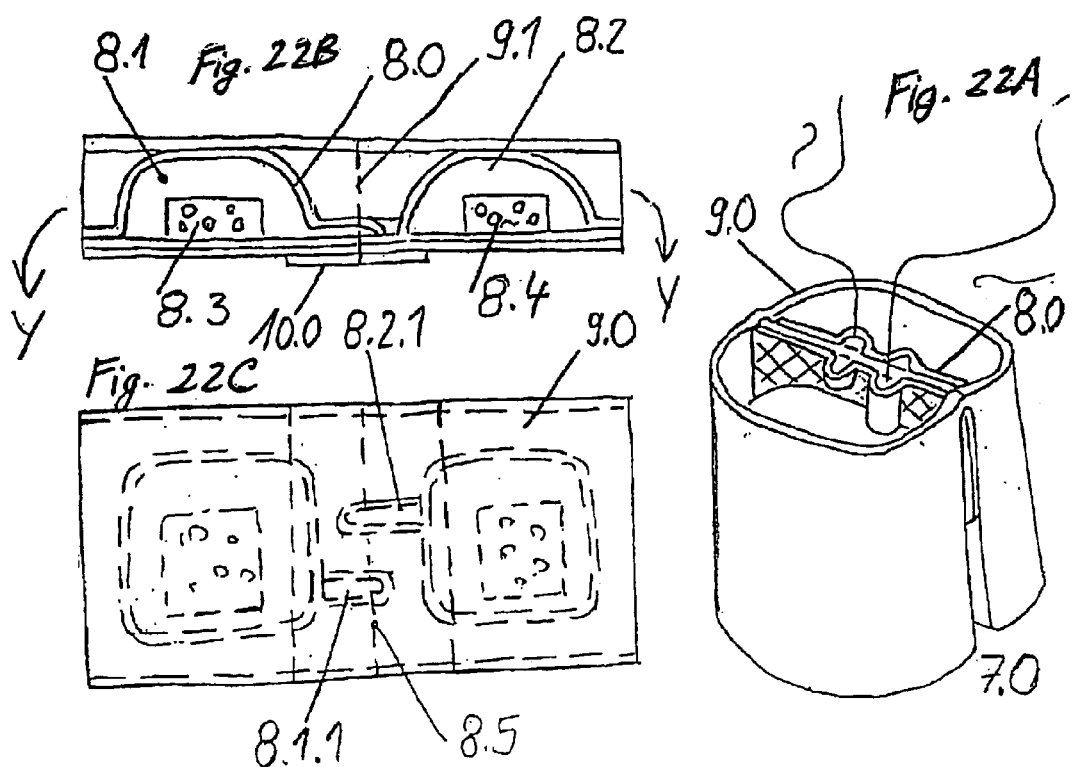

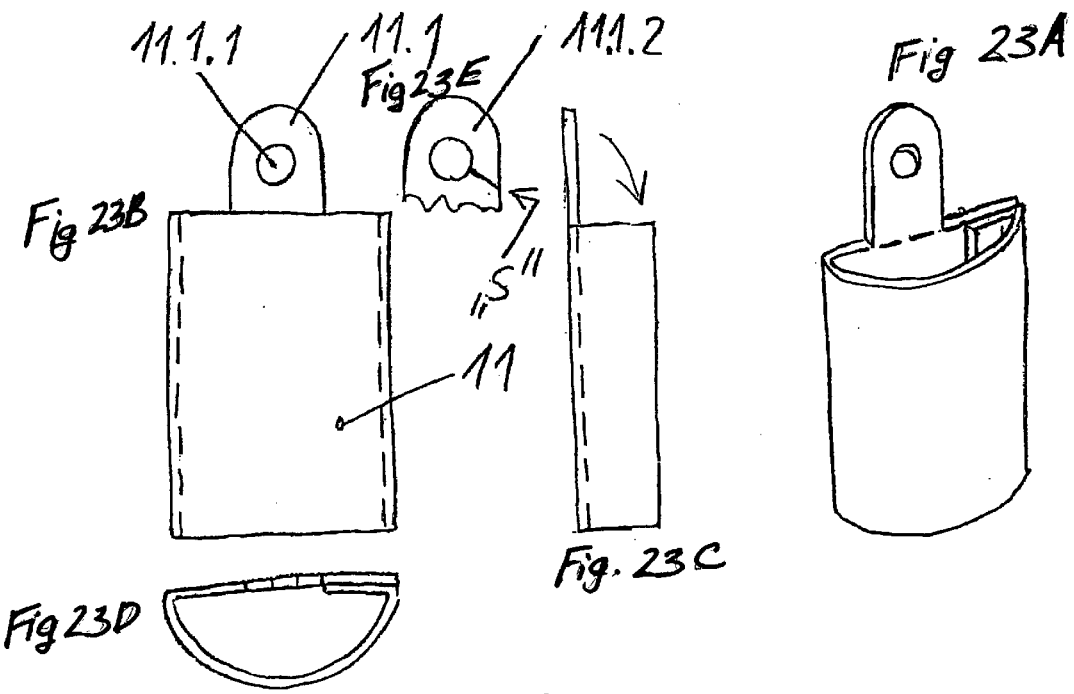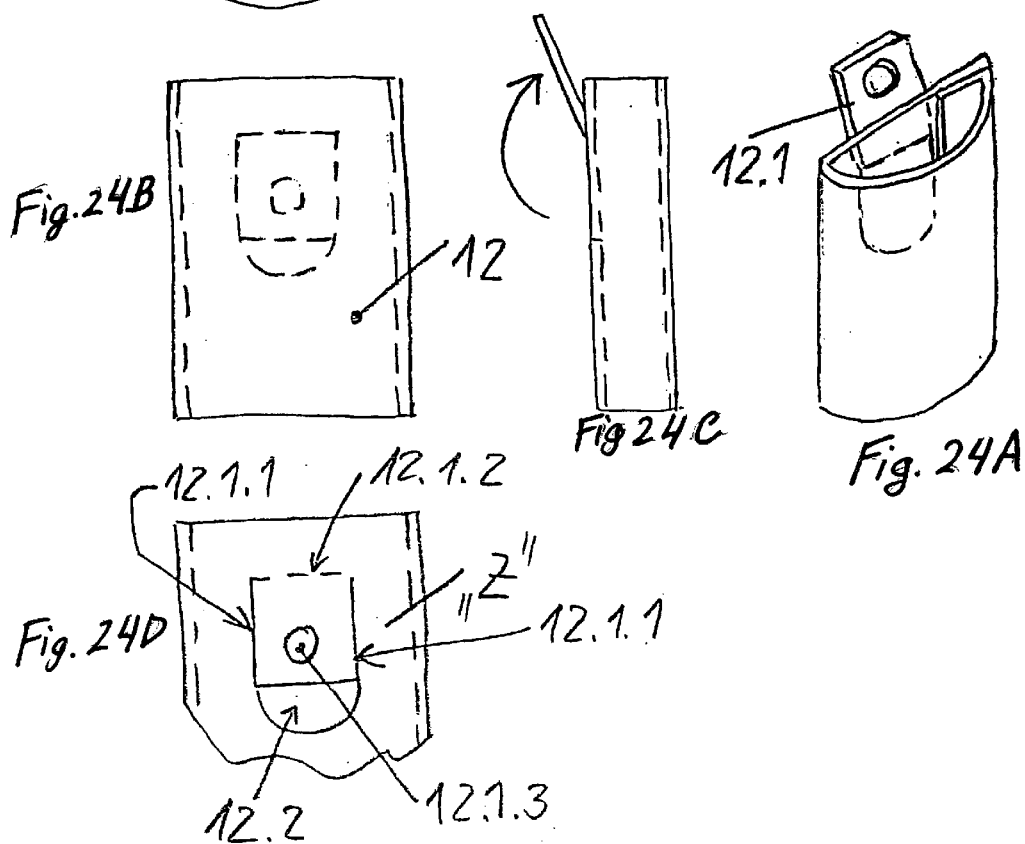

FRAGRANCE DISPENSER

BACKGROUND OF THE INVENTION

The present invention relates to a fragrance dispenser for dispensing perfume and other scent carriers.

People perceive objects and other people to a significant degree in part through their sense of smell, and their behavior is profoundly affected by this. Even small concentrations of aromas can influence people's moods and, consequently, their behavior.

Fragrance dispensers take advantage of these biological mechanisms, be it to create a generally pleasant atmosphere, or for a deliberate commercial exploitation to effect a certain human behavior, such as, e.g., to encourage a buying mood.

This stimulating effect becomes significant especially when decisions of far-reaching consequence are to be made, for example at important conferences and meetings.

A multitude of technical packaging approaches are known that have as their purpose to create a fragrance concentration, over an extended period of time in a certain volume, that is intended to enhance the desired behavior.

A fragrance dispenser of the type under consideration is disclosed in patent document WO 00/06464, wherein a porous material that serves as storage for a liquid product is contained in a reservoir. Upon exertion of pressure onto any of the walls of the reservoir, a portion of this product is emitted into the ambient air through an opening as a spray or dispersion.

Patent document WO 00/21853 attempts to improve the aesthetic appearance of this type of fragrance dispenser in such a way that the reservoir is encompassed over a large surface by a band-like packaging element, which may contain punched out patterns and/or imprints.

BRIEF SUMMARY OF THE INVENTION

It is an object of the present invention to significantly improve the operation of fragrance dispensers of the last-named type.

This object is met, according to the invention, by a fragrance dispenser having a reservoir to receive an aroma carrier, the fragrances of which can escape at least partially through a dispensing opening when pressure is exerted onto the reservoir.

The starting point of the invention is an absorbent element, e.g., a sponge, felt, or cardboard, in a thermoformed package as a reservoir. This element serves to fully absorb an aromatic carrier substance (e.g., perfume oil). This element is significantly smaller in its volume than the space formed by the package, so that an atmosphere that is enriched with the fragrance can form inside the package. At a suitable location, the thermoformed or cover film has a small opening, which is sealed, e.g., by an adhesive label, adhesive dot, or peel-off film. This seal is removed for activation purposes. Through this opening the fragrance-enriched air can emanate from the interior of the package to the outside. Pressure that is exerted onto the package causes more intensely enriched air to flow into the environment. The shape of the thermoforming film is designed such that it regains its original shape once the pressure has been released. The air volume in the interior of the package returns to its original size by drawing in non-enriched air, which can again become enriched with fragrance. The process can then start again. Packages without this resetting function are also possible; in that case the release of aromatic substances is achieved by giving the outlet opening an appropriate size so that the air circulation is suitably modified.

The thermoformed package that serves as a reservoir may be enclosed, according to one embodiment of the invention, with a packaging element, preferably one that is composed of a band-like enclosure made of a sealable carton. This enclosure serves to provide an optical optimization, and as a carrier for advertising texts and a functional description, and to support the technical function.

In a further improvement, provision may be made for supplementing and enhancing this display function of the band-like enclosure in such a way that the enclosure is given also technical functionality in the activation of the fragrance dispenser, specifically in the form of an interaction with the seal of the thermoformed package.

BRIEF DESCRIPTION OF THE DRAWINGS

A number of embodiments will be explained in more detail with reference to the following drawings.

FIGS. 1A, 1B and 1C are, respectively, a top view and left and right cross-sectional views through a first embodiment of a fragrance dispenser according to the invention.

FIG. 2A shows a top view of a variation of the first embodiment and FIG. 2B is a detail view of part of the variation of FIG. 2A.

FIGS. 5A and 5B are, respectively, a top view and section through a third embodiment.

FIG. 6 illustrates the function of the third embodiment.

FIG. 7 is a top view and section through a fourth embodiment.

FIG. 7A is a detail view of a modified part of the fourth embodiment.

FIG. 8 illustrates the function of the fourth embodiment.

FIG. 11 is an illustration of a seventh embodiment in perspective.

FIGS. 12A and 12B are, respectively, a longitudinal section and top view of the thermoformed package of the fragrance dispenser according to FIG. 1 without a band-like enclosure.

FIGS. 13A, 13B and 13C are, respectively, a longitudinal section, a top view and an end section of the fragrance dispenser according to FIG. 11 with a band-like enclosure.

FIGS. 14A and 14B show two sections illustrating the function of the fragrance dispenser according to FIGS. 11–13.

FIGS. 15A–C, 16A–C, 17A–C and 18A–C show partial sections through variations of the seventh embodiment with recloseable seals.

FIGS. 19A–C and 20A–C show partial sections through variations with non-recloseable seals.

FIGS. 21A–C and 22A–C show sections and an illustration in perspective of an eighth embodiment of the fragrance dispenser as a thermoformed snap-off package.

FIGS. 23A–E and 24A–D are illustrations showing designs of the packaging element.

DETAILED DESCRIPTION OF THE INVENTION

Figures 3A, 3B, 3C:
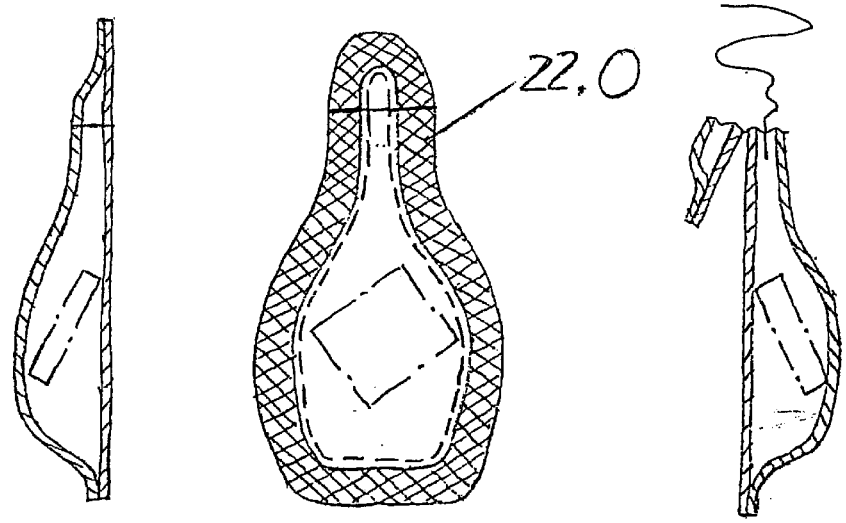
FIGS. 3A, 3B and 3C are, respectively, a top view and left and right cross-sectional views through a second embodiment.

FIGS. 1A, 1B and 1C show, as a first embodiment, a fragrance dispenser 20.0, the basic design of which corresponds to the design of a thermoformed package 2.0 that will be described below with reference to FIGS. 11 through 13. The use of the fragrance dispenser 20.0 without an additional packaging element as external packaging allows for a wide range of designs of the thermoformed bowl 20.1 thereof, which may be modeled on a commercially available product, such as, e.g., a perfume bottle. The dispensing opening 20.2 for fragrance from the thermoformed package 20.0 is initially sealed by means of an adhesive label 20.3. The adhesive label 20.3 is coated with adhesive in the region k; a one-sided extension 1 is not coated with adhesive and serves as a pull tab. The opening 20.2 and the adhesive label 20.3 may also be affixed on a flat cover film 20.4. To secure the fragrance dispenser, e.g., on a tile, an adhesive patch, or disc, 20.5 is affixed on a suitable place on the fragrance dispenser 20.0. The fragrance dispenser contains a porous element 20.6 impregnated with an aromatic carrier substance.

The fragrance dispenser 21.0 according to the variation in FIGS. 2A and 2B is identical in its basic design with the fragrance dispenser 20.0. The fragrance dispenser 21.0 is elongated in its sealing area, where it has a punched out section 21.1 from which the fragrance dispenser may be hung. A cut 21.2 or also an additional punched out section, may be provided between the punched out section 21.1 and the outer contour of the fragrance dispenser, which permits the fragrance dispenser to be hung to a closed system.

FIGS. 3A, 3B and 3C show, as a second embodiment, a fragrance dispenser 22.0 in the form of a thermoformed snap-off package as will be described below with reference to FIG. 21. As a fragrance dispenser without external packaging it thus also offers the widest possible range of design options, like the fragrance dispenser 20.0 described with reference to FIGS. 1.

Figures 4A, 4B:
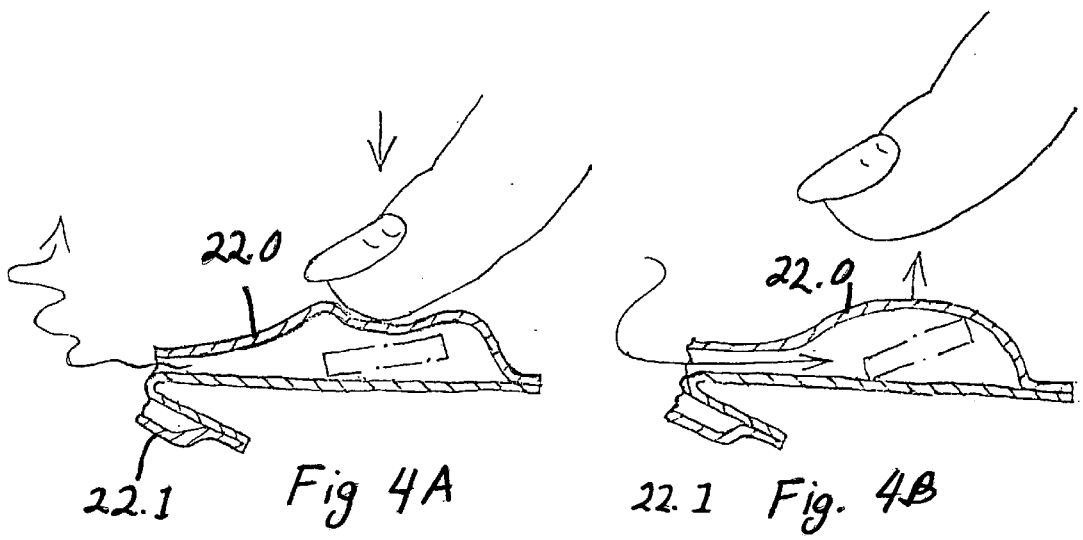
FIGS. 4A and 4B illustrate the function of the second embodiment.

FIGS. 4A and 4B show the function of the thermoformed snap-off package 22.0; the fragrance medium emanates after the nose 22.1 is snapped off, as will be explained in greater detail below with reference to FIG. 11. In FIG. 4A, the package is being compressed and fragrance is being emitted. In FIG. 4B, pressure has been released and fresh air is flowing into the package.

FIGS. 5A and 5B show, as a third embodiment, a fragrance dispenser 24.0 in the form of a thermoformed snap-off package without external packaging and with two thermoformed bowls. The basic design corresponds to the package 8.0 to be described below with reference to FIGS. 12. To initiate the snap-off function, the thermoformed snap-off package is provided with indentations 24.2.1 and 24.2.2 in the region of a scored line area 24.1. The scored area 24.1 extends through at least one snap-off nose 24.3, 24.4 in such a way that an interconnected free-standing package with free dispensing opening(s) is obtained after the bending FIG. 6 shows the fragrance dispenser 24.0 in its activated and stand-up position after it has been snapped open to provide openings at noses 24,3 and 24.4.

FIG. 7A shows, as a fourth embodiment, a fragrance dispenser 26.0. Its basic design is identical to that of the fragrance dispenser 24.0, but is extended, on one side, by a tab 26.1.1, which is delimited against the actual package by a perforation, scoring, or embossed line 26.2. The perforation, scoring, or embossed line 26.2 is provided with indentations 26.3.1.and 26.3.2 to facilitate its bending. The tab 26.1.1 has on its edge a cutout 26.4.1. Cutout 26.4.1 may be replaced by a cutout 26.4.2 that is open towards the outer contour of the dispenser, as shown in FIG. 7B. On the opposite side, the fragrance dispenser 26.0 has a projection 26.6 that is aligned with cutout 26.4.1 or 26.4.2. The cutout 26.4.1 or 26.4.2 and the projection 26.6 may be provided either on the tab or on the package.

FIG. 8 shows the fragrance dispenser 26.0 in its activated condition. To activate the fragrance dispenser, it is snapped open along its scoring 26.5; the tab 26.1.1 is bent around its perforation line 26.2 and is locked into the cutout 26.4.1 or 26.4.2, so that a triangular structure with a stable base results.

Figure 9:
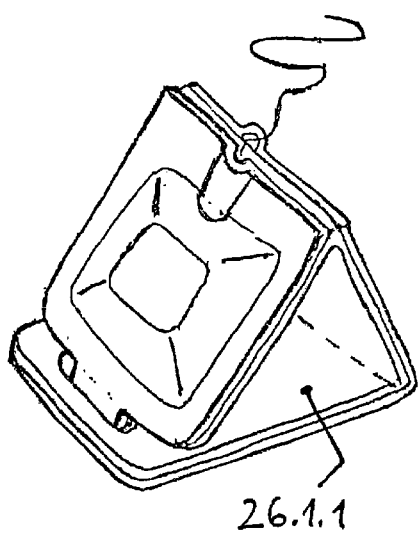
FIG. 9 illustrates the function of a fifth embodiment.

A fifth embodiment of the fragrance dispenser 26.0 is shown in FIG. 9 and is provided with only one thermoformed bowl. The region between the scoring 26.5 and perforation 26.2 thus serves only as a firm base. The thermoformed bowl may also be disposed in the region between the scoring 26.5 and perforation 26.2.

Figure 10:
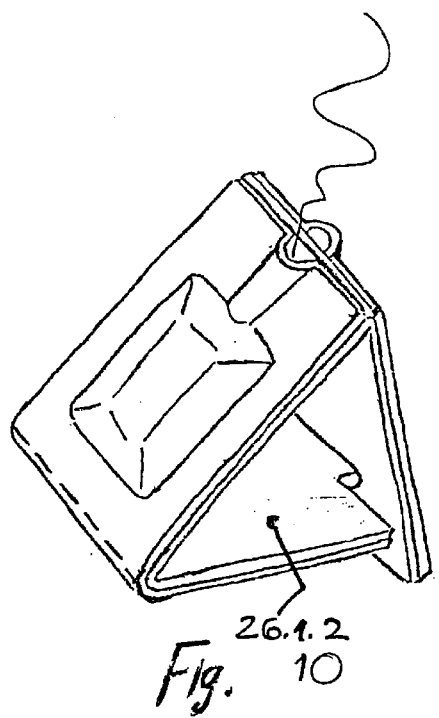
FIG. 10 illustrates the function of a sixth embodiment.

FIG. 10 shows a variation presented as a sixth embodiment with reversed positions of the cutout 26.4 and projection 26.6.

In the embodiments that will be described below, the fragrance dispenser is enclosed by an additional packaging element serving as an external package FIG. 11 shows, as a seventh embodiment, a perspective view of a fragrance dispenser 1.0 in its activated condition. This dispenser includes a thermoformed package 2.0 that is shown in FIGS. 12. FIGS. 13 show the complete package.

The fragrance dispenser 1.0 is composed of a thermoformed package 2.0 as a reservoir and a packaging element 3.0 in the form of a band-like enclosure. The thermoformed package 2.0 consists of a thermoplastically shaped thermoforming film 2.1 and cover film 2.2. The thermoforming film 2.1 is shaped such that it regains its original shape after it has been deformed to release the fragrance. The cover film 2.2 is sealed onto the thermoforming film 2.1 to form a gas-tight enclosure that encloses a hollow space 2.4. Into the hollow space 2.4 a porous element 2.5 is placed, element 2.6 being wetted with a liquid fragrance carrier prior to sealing the cover film 2.2 onto the thermoforming film 2.1. The thermoformed package 2.0 is extended on one side with a projection 2.6. The air in the hollow space 2.4 becomes enriched with the fragrance molecules that escape from the porous element 2.5. The thermoformed package is penetrated by an outlet opening 2.7 that is sealed with a sealing element, such as, e.g., an adhesive disc 2.8, or by means of an adhesive label (not shown here), until it is activated.

The thermoformed package 2.0 is enclosed by a band-like enclosure 3.0, preferably of paper or cardboard, in such a way that the edge region in an area of overlap 3.1 (FIGS. 13B and 13C) of the band-like enclosure 3.0 is sealable. The connection in the area of overlap 3.1 may be created either by sealing or by gluing. The dimension LT of the thermoformed package 2.0 is generally identical to or smaller than the dimension LB of the band-like enclosure 3.0 so that the thermoformed package 2.0 does not protrude out of enclosure 3.0.

To this extent the basic design of the embodiments already described is largely identical. The embodiments differ in the design of the opening region regarding its cooperation between the band-like enclosure and thermoformed package, as will be explained below In the region of the closed outlet opening 2.7, the band-like enclosure 3.0, in this embodiment, has two perforations 3.2 parallel to the longitudinal axis of the package.

The perforations 3.2 are connected at their ends by an additional perforation or embossed line 3.3, which extends perpendicular to the longitudinal axis.

To activate the fragrance dispenser 1.0, the center section 3.5 of the band-like enclosure 3.0 is pulled open along the perforations 3.2, removing disc 2.8 from opening 2.7. The embossed line 3.3 serves as a hinge. The adhesive for the adhesive disc 2.8 (or label) is selected such that its adhesion to the band-like enclosure 3.0 is greater than its adhesion to the thermoformed package 2.0. After flipping up the center section 3.5 of the band-like enclosure 3.0 the fragrance dispenser is thus open.

Utilization of the package of FIGS. 11–13 is illustrated in FIGS. 14A and 14B. As shown in FIG. 14A, once the fragrance dispenser 1.0 is open, the emission of aromatized air L1 can be increased by exerting pressure onto the band-like enclosure 3.0. After the pressure has been released, as shown in FIG. 14B, the thermoforming film 2.1 of the thermoformed package 2.0 regains its original shape and non-aromatized air L2 can flow into the thermoformed package. To reseal the package, the center region 3.5 is pressed against the deep drawn package 2.0. The process can now repeat itself.

FIGS. 15A, 15B and 15C show, respectively, a top view and two sectional views of a first variation of the seal area of the seventh embodiment, similar to the variation shown in FIGS. 11–13. For improved handling, the center region 3.5 between the perforation lines is designed as a projecting tab in this embodiment.

In a second variation shown in FIGS. 16A, 16B and 16C, which are, respectively, a top view and two sectional views, the tab 3.5 of the band-like enclosure 3.0 has been moved inward; to make the tab 3.5 easier to grasp a cutout 3.6 has been punched out in the lower adjoining area. The sides of the tab 3.2 may be either punched or perforated. To open the fragrance dispenser 1.0, the tab 3.5 is grasped through the cutout 3.6 and pulled up. To reclose the package 1.0, the tab 3.5 is pushed back into its original position.

In a third variation-according to FIGS. 17A, 17B and 17C, which are, respectively, a top view and two sectional views, the band-like enclosure 3.0 has a punched out hole 3.7 in the region of the outlet opening 2.7 of the thermoformed package 2.0. The outlet opening 2.7 is covered with the aid of an adhesive label 3.8 as a seal, with the dimension a of the label 3.8 being smaller than the dimension b of the punched out hole. The region c of the label 3.8 is coated with adhesive on the area that is in contact with the thermoformed package 2.0. The region d of the adhesive label 3.8 is free of adhesive and formed into a tab that may be folded over. In the region e the adhesive label extends underneath the band-like enclosure 3.0 so that a locking point results when the label is removed. For resealing, the label 3.8 is pushed back.

In a fourth variation according to FIGS. 18A, 18B and 18C, which are, respectively, a top view and two sectional views, the outlet opening 2.7 of the thermoformed package 2.0 is sealed with an adhesive label 3.8. In the region of the adhesive label 3.8 the band-like enclosure 3.0 has two perforation lines 3.2, with the perforation spacing f being larger than the width a of the adhesive label 3.8. The perforation lines 3.2 are connected by a perforation or embossed line 3.3 that serves as a hinge. The adhesive label 3.8 extends beyond the embossed line 3.3 by the dimension g and can thus not be completely removed. The grasping area h of the adhesive label 3.8 is free of adhesive. To open the fragrance dispenser, the region between the two perforation lines 3.8 is held and pulled open along the perforation lines 3.2 to the embossed line 3.3, and the fragrance dispenser is thus opened. To close it, the pulled-open section is pushed back into its original position.

FIGS. 19A, 19B and 19C, which are, respectively, a top view and two sectional views, show, as a fifth variation, a non-recloseable opening variation of the fragrance dispenser 1.0. The outlet opening 2.7 of the package 2.0 is sealed with an adhesive label 3.8. In the region of the outlet opening 2.7 the band-like enclosure 3.0 has a punched out hole 3.9 that is a little larger than the outlet opening 2.7 of the thermoformed package 2.0. The adhesive-free area i of the label is folded over and extends beyond the end of the package. The label 3.8 can be removed by pulling on its pull tab 3.8.1.

A sixth variation according to FIGS. 20A, 20B and 20C, which are, respectively, a top view and two sectional views, essentially contains the characteristics as they have been described with reference to FIG. 19. However, the pull tab 3.8.1 does not project beyond the package 1.0. To make the pull tab 3.8.1 easier to grasp, a cutout 3.9 is provided in the edge region of the band-like enclosure.

FIGS. 21A, 21B and 21C, which are, respectively, a perspective view, a sectional view and a top view, show, as an eighth embodiment, a fragrance dispenser 4.0; it is based on a thermoformed snap-off package 5.0 as it is already in use for other products; therefore it will not be described in detail. Provided in the thermoformed snap-off package 5.0 is an element 5.3 that is wetted with a liquid fragrance carrier, as described with reference to FIGS. 11–14. The reservoir 5.0 is also encompassed by a band-like enclosure, the basic design of which is described with reference to FIGS. 11–13. In the region of a breakaway seam 5.1, which extends over a snap-off nose 5.2 of the thermoformed snap-off package 5.0, the band-like enclosure 6.0 has a circumferential perforation 6.1.

For activation purposes, the band-like enclosure 6.0 with the enclosed thermoformed snap-off package 5.0 is snapped open in the direction of the arrow z.

FIGS. 22A, 22B and 22C, which are, respectively, a perspective view, a sectional view and a top view, show a variation of the fragrance dispenser as described with reference to FIGS. 21, with a reservoir in the form of a thermoformed snap-off package 8.0 with two thermoformed bowls 8.1 and 8.2, each equipped with an absorbent element 8.3 and 8.4 to receive identical or different aroma carriers. Two snap-off noses 8.1.1 and 8.2.1 are arranged towards the center, offset from one another. In the center a scoring 8.5 extends over the thermoformed snap-off package 8.0 and its snap-off noses 8.1.1 and 8.2.1 as a desired breakaway point. The thermoformed snap-off package 8.0 is also encompassed by a band-like enclosure 9.0. In the center, and thus located above the snap-off scoring 8.5 of the thermoformed package 8.0, the band-like enclosure 9.0 has a circumferential perforation 9.1. On the underside of the package 7.0 an adhesive label 10.0 is affixed in such a way that its side that faces away from the package adheres only to itself.

For activation purposes, the two package ends are bent in the direction of the arrows y and the band-like enclosure 9.0 and thermoformed snap-off package 8.0 are thus snapped open. The adhesive label 10.0, which is also joined in the process, connects onto itself and holds the bent package 7.0 in its position; it can now easily be stood on its front ends. The two snapped open snap-off noses 8.1.1 and 8.2.1 allow the fragrances to escape and mix together.

FIGS. 23A, 23B, 23C, 23D and 23E, which are, respectively, a perspective view, a top view, a side view, an end view and detail view, and FIGS. 24A, 24B, 24C and 24D, which are, respectively, a perspective view, a top view, a side view and detail view, show further developments of the fragrance dispenser outside the opening area.

In FIGS. 23, the band-like enclosure 11 is extended by a tab 11.1 that has a punched out hole 11.1.1 and thus provides an option to hang the package. In FIG. 23E, tab 11.1 is replaced by a tab 11.1.2 provided with an additional punched out line s for easier hanging.

In the variation according to FIGS. 24, the tab 12.1 is integrated on the rear of the package. FIG. 24D shows, in region z, the band-like enclosure 12 from behind. The side shape 12.1.1 of the tab 12.1 is perforated and pre-punched. The two side perforations 12.1.1 are joined at their upper ends by a further perforation or embossed edge 12.1.2, the pre-perforated tab 12.1 has a punched hole 12.1.3 that permits a later hanging. In the region of what will later be the tab end, a punched hole 12.2 is provided, which is to facilitate grasping of the tab. To hang the dispenser, the tab 12.1 is grasped through the punched out section 12.2 and bent back and up over the embossed edge 12.1.2. The bent tab 12.1 extends beyond the band-like enclosure 12 and thus offers an option to hang the fragrance dispenser.

This application relates to subject matter disclosed in German Application Number 201 14 352.6, filed on Aug. 30, 2001, the disclosure of which is incorporated herein by reference.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A fragrance dispenser having a reservoir to receive an aroma carrier, said dispenser having a dispensing opening through which fragrances can escape from the reservoir at least partially through when pressure is exerted onto the reservoir, wherein said dispenser further comprises a packaging element that extends beyond the dispensing opening of the reservoir and is shaped in an area of that opening in such a way that said packaging element cooperates with a seal of the dispensing opening of the reservoir.

2. The fragrance dispenser according to claim 1, wherein the seal of the dispensing opening comprises a sealing element (2.8) disposed in a region of the dispensing opening (2.7) to cover the dispensing opening, and wherein said packaging element comprises an actuation means having an underside to which said sealing element is connected so that, when the actuation means is opened, the sealing element (2.8) adheres to the actuation means and unblocks the dispensing opening (2.7).

3. The fragrance dispenser according to claim 2, wherein the actuation means is constituted by a tab (3.5) that is defined by perforation lines (3.2) of the packaging element.

4. The fragrance dispenser according to claim 3, wherein the tab (3.5) extends beyond one edge of the packaging element.

5. The fragrance dispenser according to claim 2, wherein the sealing element is an adhesive label (3.8).

6. The fragrance dispenser according to claim 2, wherein the packaging element is a band-like enclosure (3.0) that encloses the reservoir.

7. The fragrance dispenser according to claim 6, wherein the band-like enclosure (3.0) is formed of a sealable cardboard cutout.

8. The fragrance dispenser according to claim 1, wherein a cutout (3.7) is provided in the packaging element that incorporates the dispensing opening (2.7) and into which a seal, specifically a movable seal, projects that is held between the packaging element and reservoir.

9. The fragrance dispenser according to claim 8, wherein the seal is an adhesive label (3.8) that extends beyond one edge of the packaging element and that can be pulled out from the packaging element between the packaging element and reservoir.

10. The fragrance dispenser according to claim 8, wherein the seal is an adhesive label (3.8) that extends into a cutout (3.9) on the edge of the packaging element and that can be pulled out from the packaging element.

11. The fragrance dispenser according to claim 1, wherein the packaging element incorporates a perforation (5.1) extending over a snap-off nose (5.2) of the reservoir, which snap-off nose opens when the perforation (5.1) is pulled open.

12. The fragrance dispenser according to claim 11, wherein: wherein the reservoir is a thermoformed package (2.0), comprising a thermoformed element (2.1) of thermoplastically shaped plastic film and a cover film (2.2) sealed onto said thermoformed element; the packaging element is a band-like enclosure (3.0) that encloses the reservoir; and the band-like enclosure (3.0) has an overlapping area (3.1) in the region of the cover film (2.2) of the thermoformed package (2.0), which is glueable or sealable.

* * * * *